(12) United States Patent
Lakhotia et al.

(10) Patent No.: US 7,553,634 B1
(45) Date of Patent: Jun. 30, 2009

(54) EXTRACTION OF INTEGRAL MEMBRANE PROTEINS

(75) Inventors: Sanjay Lakhotia, Danville, CA (US); Michael R. Biehl, Sanford, NC (US)

(73) Assignee: Wyeth Holdings Corporation, Madison, NJ (US)

( * ) Notice: Subject to any disclaimer, the term of this patent is extended or adjusted under 35 U.S.C. 154(b) by 743 days.

(21) Appl. No.: 10/019,163

(22) PCT Filed: Jun. 20, 2000

(86) PCT No.: PCT/US00/17019

§ 371 (c)(1), (2), (4) Date: Dec. 20, 2001

(87) PCT Pub. No.: WO01/00668

PCT Pub. Date: Jan. 4, 2001

(51) Int. Cl.
*C12P 1/00* (2006.01)
*A61K 39/00* (2006.01)
*A61K 39/21* (2006.01)

(52) U.S. Cl. ............ 435/41; 424/184.1; 424/208.1

(58) Field of Classification Search .......... 424/184.1, 424/206.1; 435/41, 69.1; 530/300, 350
See application file for complete search history.

(56) References Cited

U.S. PATENT DOCUMENTS

| | | | | |
|---|---|---|---|---|
| 5,098,997 A | * | 3/1992 | Anilionis et al. | 530/350 |
| 5,110,908 A | * | 5/1992 | Deich et al. | 530/403 |
| 5,276,141 A | * | 1/1994 | Kolbe | 530/395 |
| 5,601,831 A | | 2/1997 | Green et al. | |
| 5,681,570 A | | 10/1997 | Yang et al. | |
| 5,681,936 A | * | 10/1997 | Nicholson | 530/416 |
| 5,780,601 A | * | 7/1998 | Green et al. | 530/412 |

FOREIGN PATENT DOCUMENTS

| | | | |
|---|---|---|---|
| EP | 0389 925 | * | 10/1990 |
| EP | 0389925 A1 | | 10/1990 |

OTHER PUBLICATIONS

Yan-Ping et al (Vaccine, vol. 15, No. 9, p. 976-987, 1997).*
Green et al (Infection and Immunity, Sep. 1991, p. 3191-3198).*
van Reis (Biotechnology and Bioengineering, vol. 38, p. 413-422, 1991).*
Datar, (Biotechnology Letters, vol. 7, No. 7, p. 471-476, 1985).*
Reis, Robert van et al., "Industrial Scale Harvest of Proteins from Mammalian Cell Culture by Tangential Flow Filtration", J. Biotechnology and Bioengineering, 38/4 (413-422) ISSN: 0006-3592 (1991).
Guzman Luz-Marie et al., "Tight Regulation, Modulation, and High-Level Expression by Vectors Containing the Arabinose Pbad Promoter" J. of Bacteriology, 177/14 (4121-4130) ISSN: 0021-9193 (1995).
Werner R.G. et al., "Purification of Proteins Produced by Biotechnological Process" Arzneimittel-Forschung/Drug Research, 38/3 (422-428) ISSN 0004-4172 (1998).

* cited by examiner

*Primary Examiner*—N. M. Minnifield
*Assistant Examiner*—Vanessa L. Ford
(74) *Attorney, Agent, or Firm*—Joel Silver; Alan Gordon; Michael Moran

(57) ABSTRACT

A process is described for extracting gram-negative integral membrane proteins from bacteria or bacterial host cells containing a recombinant vector by differential detergent tangential flow diafiltration. This process has several advantages over alternate processes. First, it combines the clarification and extraction processes into one unit operation. The product is extracted from the cells and it is separated from cell debris with only one continuous diafiltration process. Second, the membrane proteins are extracted in a semi-purified state, which simplifies the downstream processing steps. Third, this process is very scalable because the only requirement is that the surface area of the membranes be increased proportionally with the amount of cells.

16 Claims, 4 Drawing Sheets

EXTRACTION OF INTEGRAL MEMBRANE PROTEINS

FIELD OF THE INVENTION

This invention is directed to a process for extracting gram-negative integral membrane proteins from bacteria or bacterial host cells containing a recombinant vector by differential detergent tangential flow diafiltration.

BACKGROUND OF THE INVENTION

Gram-negative bacteria possess both an inner membrane and an outer membrane. Collectively, the proteins contained in these membranes are referred to as integral membrane proteins. Native integral membrane proteins can be extracted from gram-negative bacteria in relatively small quantities. Recombinant expression techniques permit these proteins to be expressed from bacteria in increased quantities.

Small scale batch purification of such native or recombinant integral membrane proteins has involved an extraction step utilizing centrifugation to extract protein from bacterial cell lysate, followed by downstream purification using conventional techniques.

However, centrifugation is not preferred for extraction of such proteins on a larger scale, because it is a cumbersome process. A larger scale extraction process is desirable in order to obtain quantities of proteins sufficient for economical manufacturing.

Thus, there is a need for a process for extracting native or recombinant gram-negative integral membrane proteins which avoids the use of centrifugation and is therefore more amenable to scale-up. Two such proteins are the lipidated outer membrane proteins P4 and P6 of *Haemophilus influenzae*.

SUMMARY OF THE INVENTION

Thus, it is an object of this invention to develop a process for extracting native or recombinant gram-negative integral membrane proteins which avoids the use of centrifugation and is therefore more amenable to scale-up.

It is another object of this invention to develop a process for selectively solubilizing inner and outer membrane proteins of gram-negative bacteria.

It is a further object of this invention to develop processes for extracting the lipidated forms of the recombinant *H. influenzae* outer membrane proteins P4 and P6 from *E. coli*.

These and other objects of the invention as discussed below are achieved by processes which utilize differential detergent tangential flow diafiltration and avoid the use of centrifugation. These processes also provide for continuous extraction of desired proteins.

For the extraction of native or recombinantly-expressed, gram-negative inner membrane proteins from bacteria or bacterial host cells containing a recombinant vector, respectively, by differential detergent tangential flow diafiltration, a process is used which comprises:

(a) lysing bacteria or bacterial host cells containing a recombinant vector in a fermentation broth;

(b) diafiltering the lysed fermentation broth from (a) with a buffer which is not retained by the diafiltration membrane, wherein said buffer removes intracellular and extracellular contaminants through the permeate, and using a chelating agent to prevent proteolysis;

(c) diafiltering the lysate from (b) with a detergent and a buffer which is not retained by the diafiltration membrane, wherein said detergent solubilizes and removes inner membrane proteins, and using a divalent cation to stabilize the outer membrane proteins, thereby preventing their solubilization; and (d) collecting the inner membrane proteins removed in (c).

For the extraction of native or recombinantly-expressed, gram-negative outer membrane proteins from bacteria or bacterial host cells containing a recombinant vector, respectively, by differential detergent tangential flow diafiltration, a process is used which comprises:

(a) lysing bacteria or bacterial host cells containing a recombinant vector in a fermentation broth;

(b) diafiltering the lysed fermentation broth from (a) with a buffer which is not retained by the diafiltration membrane, wherein said buffer removes intracellular and extracellular contaminants through the permeate, and using a chelating agent to prevent proteolysis;

(c) diafiltering the lysate from (b) with a detergent and a buffer which is not retained by the diafiltration membrane, wherein said detergent solubilizes and removes inner membrane proteins, and using a divalent cation to stabilize the outer membrane proteins, thereby preventing their solubilization;

(d) diafiltering the lysate from (c) with the buffer from (c), and using a divalent cation from (c) in the absence of detergent, in order to reduce the concentration of the detergent from (c);

(e) diafiltering the lysate from (d) with a buffer which is not retained by the diafiltration membrane, a chelating agent and a detergent to solubilize and remove the outer membrane proteins; and (f) collecting the outer membrane proteins removed in (e).

If desired, further extraction can be performed by adding the following steps to the foregoing process:

(g) diafiltering the lysate from (e) with reagents of (e), with the exception of the detergent, in order to reduce the concentration of the detergent;

(h) diafiltering the lysate from (g) with reagents of (e); and (i) collecting the outer membrane proteins removed in (h).

For the extraction of lipidated recombinant, outer membrane protein P4 (lipidated rP4) of *H. influenzae* from bacterial host cells by differential detergent tangential flow diafiltration, a process is used which comprises:

(a) lysing bacterial host cells in a fermentation broth;

(b) diafiltering the lysed fermentation broth from (a) with a buffer which is not retained by the diafiltration membrane, wherein said buffer removes intracellular and extracellular contaminants through the permeate, and using a chelating agent to prevent proteolysis;

(c) diafiltering the lysate from (b) with a detergent and a buffer which is not retained by the diafiltration membrane, wherein said detegent solubilizes and removes inner membrane proteins, and using a divalent cation to stabilize the outer membrane proteins, thereby preventing their solubilization;

(d) diafiltering the lysate from (c) with the buffer from (c), and using a divalent cation from (c) in the absence of detergent, in order to reduce the concentration of the detergent from (c);

(e) diafiltering the lysate from (d) with a buffer which is not retained by the diafiltration membrane, a chelating agent and a detergent to solubilize the outer membrane proteins;

(f) diafiltering the lysate from (e) with a buffer which is not retained by the diafiltration membrane, a chelating agent and a detergent to extract and remove the lipidated rP4; and (g) collecting the lipidated rP4 removed in (f).

If desired, further extraction of lipidated rP4 can be performed by adding the following steps to the foregoing process:

(h) diafiltering the lysate from (f) with reagents of (f), with the exception of the detergent, in order to reduce the concentration of the detergent;

(i) diafiltering the lysate from (h) with reagents of (f) to extract and remove the lipidated rP4; and (j) collecting the lipidated rP4 removed in (i).

If also desired, still further extraction of lipidated rP4 can be performed by adding the following steps to the foregoing process:

(k) diafiltering the lysate from (j) with reagents of (f), with the exception of the detergent, in order to reduce the concentration of the detergent;

(l) diafiltering the lysate from (k) with reagents of (f) to extract and remove the lipidated rP4; and (m) collecting the lipidated rP4 removed in (l).

Still further cycles of lipidated rP4 extraction may be utilized, if desired.

For the extraction of lipidated recombinant, outer membrane protein P6 (lipidated rP6) of *H. influenzae* from bacterial host cells by differential detergent tangential flow diafiltration, a process is used which comprises:

(a) lysing bacterial host cells in a fermentation broth;

(b) diafiltering the lysed fermentation broth from (a) with a buffer which is not retained by the diafiltration membrane, wherein said buffer removes intracellular and extracellular contaminants through the permeate, and using a chelating agent to prevent proteolysis;

(c) diafiltering the lysate from (b) with a detergent and a buffer which is not retained by the diafiltration membrane, wherein said detergent solubilizes and removes inner membrane proteins, and using a divalent cation to stabilize the outer membrane proteins, thereby preventing their solubilization;

(d) diafiltering the lysate from (c) with a buffer which is not retained by the diafiltration membrane, a chelating agent to sequester divalent cation and to prevent proteolysis, and a detergent to solubilize and remove the outer membrane proteins other than lipidated rP6;

(e) diafiltering the lysate from (d) with a buffer which is not retained by the diafiltration membrane, a chelating agent to prevent proteolysis, a detergent to remove additional outer membrane proteins, and a salt to disrupt the membrane/outer membrane protein complex;

(f) diafiltering the lysate from (e) with reagents of (e), with the exception of the detergent and the salt, in order to reduce the concentration of the detergent;

(g) diafiltering the lysate from (f) with a detergent and a buffer which is not retained by the diafiltration membrane, wherein said detergent solubilizes and removes additional proteins bound to the cellular outer membrane, and using a chelating agent to prevent proteolysis;

(h) diafiltering the lysate from (g) with the buffer from (g) and the chelating agent of (g) to reduce the concentration of the detergent from (g);

(i) diafiltering the lysate from (h) with a phosphate compound and a detergent to solubilize and remove additional proteins bound to the cellular outer membrane;

(j) diafiltering the lysate from (i) with a phosphate compound to reduce the concentration of the detergent from (i);

(k) heating the lysate from (j) to remove lipidated rP6 from the membrane while diafiltering that lysate with a phosphate compound and a detergent to solubilize, extract and remove the lipidated rP6; and (l) collecting the lipidated rP6 removed in (k).

If desired, the process for extracting lipidated rP6 may be modified by concentrating the lysate from (j) before proceeding to (k).

DETAILED DESCRIPTION OF THE INVENTION

Figure 1:
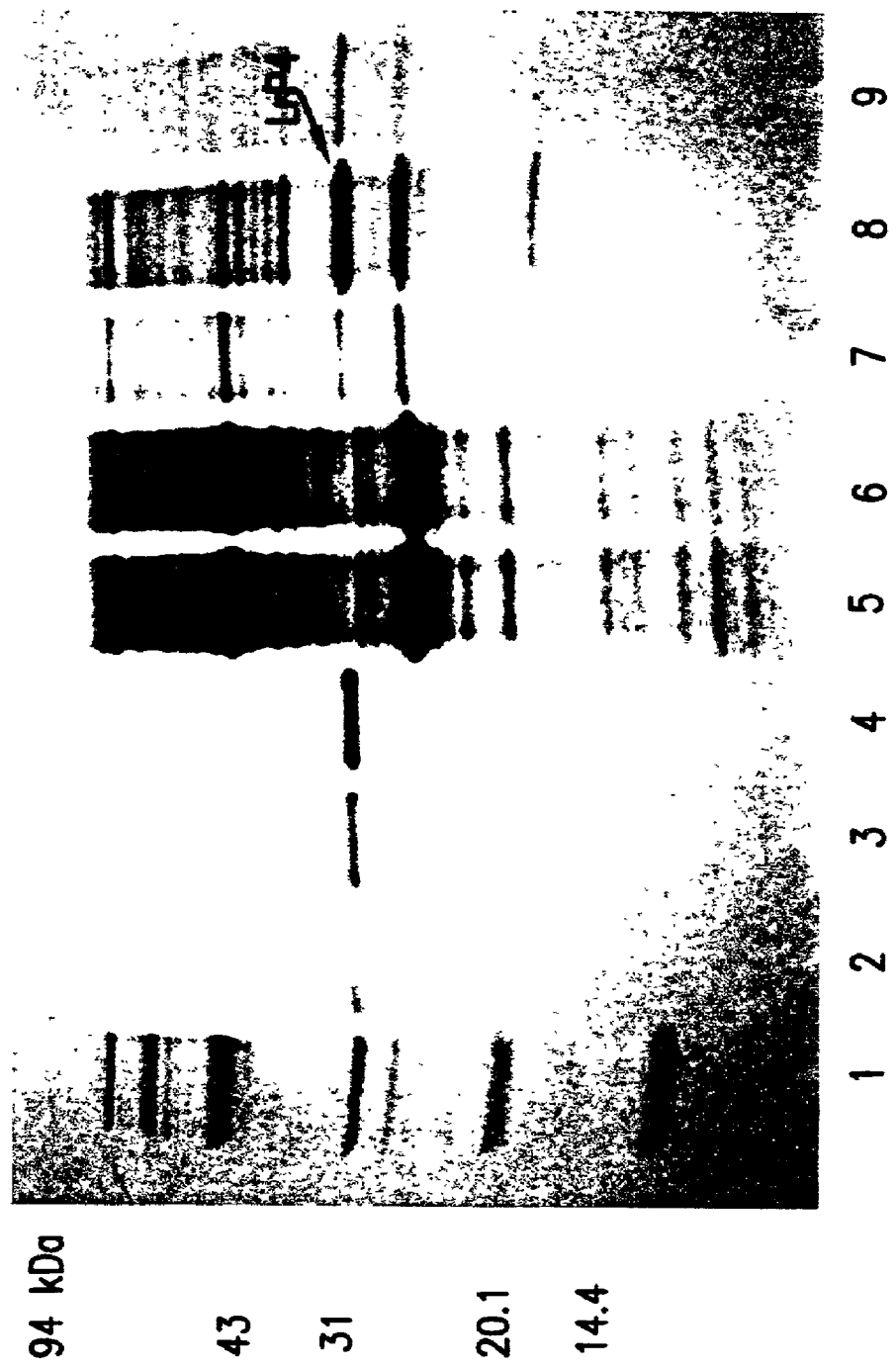
FIG. 1 depicts an SDS-PAGE analysis of samples taken from the permeate streams during the extraction process for lipidated rP4, as described in Example 1 below. Lanes: 1—Pharmacia low molecular weight markers; 2—0.1 µg lipidated rP4 standard; 3—0.3 µg lipidated rP4 standard; 4—1 µg lipidated rP4 standard; 5—Permeate from diafiltration with lysis buffer (10 mM Hepes, 1 mM EDTA); 6—Permeate from diafiltration with alpha-[4-(1,1,3,3,-tetramethylbutyl)phenyl]-omega-hydroxypoly(oxy-1,2-ethanediyl) (Triton™ X-100); 7—Permeate from diafiltration with Tris(hydroxymethyl)aminomethane (Tris™) buffer; 8—Permeate from 1× diafiltration with n-Dodecyl-N,N-dimethyl-3-ammonio-1-propanesulfonate (Zwittergent™ 3-121 buffer; 9—Permeate from 10× diafiltration with Zwittergent™ 3-12.

This process of this invention for extracting integral membrane proteins has several advantages over alternate processes. First, this process combines the clarification and extraction processes into one unit operation. The product is extracted from the cells and it is separated from cell debris with only one continuous diafiltration process. Alternative approaches typically require one unit operation for extraction and a second unit operation for clarification. The second advantage is that the membrane proteins are extracted in a semi-purified state, which simplifies the downstream processing steps. Finally, this process is very scalable because the only requirement is that the surface area of the membranes be increased proportionally with the amount of cells.

Prior to the commencement of the extraction process of this invention, an integral membrane protein from a gram-negative bacterium is expressed in a homologous or heterologous bacterial host cell by conventional methods, or the native bacterium is isolated. The fermentation broth is then lysed by passing through a homogenizer to commence the extraction process. In a preferred embodiment of this invention, the homogenizer is a microfluidizer.

The lysed fermentation broth is then subjected to a differential detergent extraction process utilizing tangential flow filtration technology. In this process the lysed cells are diafiltered with a specific sequence of buffer solutions using a tangential flow system that includes a permeable membrane with a defined size cut-off or opening. The sequence of buffer solutions is chosen to solubilize inner membrane proteins first and then to solubilize the outer membrane proteins. During diafiltration, the solubilized proteins of approximate size less than the molecular weight cut-off of the membrane pass through with the permeate, while larger molecules and unsolubilized proteins are retained.

The buffer solutions are then changed and a detergent is introduced to solubilize and extract outer membrane proteins. The sequence of buffer and detergent steps is controlled to extract the desired outer membrane protein in a selective manner. The extracted protein is then purified by conventional means such as ion exchange chromatography.

Thus, the extraction processes of this invention allow selective solubilization of inner and outer membrane proteins of gram-negative bacteria. Solubilized proteins pass through the ultrafiltration membrane with the permeate, while unsolubilized proteins are retained by the membrane.

The native integral membrane proteins extracted using this inventive process are extracted from any suitable gram-negative bacterium, including, but not limited to, *Haemophilus influenzae* (for example, the P4 and P6 proteins), *Moraxella catarrhalis* (for example, the UspA1 and UspA2 proteins), and *Neisseria meningitidis* Group B.

The recombinant integral membrane proteins extracted using this inventive process are expressed in any suitable bacterial host cell containing a recombinant vector, which in turn contains a nucleotide sequence encoding the desired recombinant integral membrane protein. Examples of such bacterial host cells include, but are not limited to, *E. coli, Salmonella, Shigella* and *B. subtilis*.

Native or recombinant proteins which have a large monomeric, multimeric or aggregate size approaching that of the membrane cut-off, should not be extracted with that membrane. However, gram-negative proteins which are expressed as inclusion bodies in *E. coli*, such as gonococcal or meningococcal proteins, may also be extracted by this process. The inclusion bodies are larger than the membrane cut-off size and are thus retained by the membrane, while other proteins are extracted. Urea or a similar denaturing agent is then added to solubilize the inclusion bodies. The desired proteins are then extracted and renatured and purified by conventional means.

The extraction process of this invention is exemplified with the recombinant forms of the P4 and P6 proteins of *Haemophilus influenzae*, as expressed in an *E. coli* host cell.

The P4 protein (also known as protein "e") of *Haemophilus influenzae* has a molecular weight of approximately 30 kD and is described in U.S. Pat. No. 5,601,831, which is hereby incorporated by reference. In its native form, the P4 protein is lipidated. In order to recombinantly express the lipidated P4 protein, the P4 gene is obtained from the bacterium and inserted into an appropriate expression vector. In examples 1 and 2 below, the expression vector pBAD18-Cm (Guzman, L.-M., et al., *J. Bacteriol.*, 177, 4121-4130 (1995)) was used. This vector contains an arabinose inducible promoter and other appropriate control elements. The expression vector is then inserted into a suitable bacterial host cell. In examples 1 and 2 below, the host cell was the *E. coli* BLR strain (Novagen, Madison, Wis.). If an inducible promoter is used, an inducer is added to cause the host cell to express the desired protein. In examples 1 and 2 below, the inducer was L-arabinose.

The P6 protein (also known as PBOMP-1 and PAL) of *Haemophilus influenzae* has a molecular weight of approximately 15 kD and is described in U.S. Pat. No. 5,110,908, which is hereby incorporated by reference. In its native form, the P6 protein is lipidated. However, previous attempts to recombinantly express lapidated rP6 resulted in low levels of expression. Copending, commonly-assigned U.S. Provisional Patent Application No. 60/141,067 describes an expression system which produces lipidated rP6. In order to recombinantly express the lipidated rP6 protein, the P6 gene is obtained from the bacterium and inserted into an appropriate expression vector. In examples 3 and 4 below, the expression vector pBAD18-CM was again used. The expression vector is then inserted into a suitable bacterial host cell. In examples 3 and 4 below, the host cell was again the *E. coli* BLR strain. If an inducible promoter is used, an inducer is added to cause the host cell to express the desired protein. In examples 3 and 4 below, the inducer was L-arabinose.

In a preferred embodiment of this invention, the diafiltration membrane is from Millipore (Bedford, Mass.). This membrane is made from regenerated cellulose, has a 1000 kD size cut-off and has a surface area of 0.002 $m^2$/g wet weight cells.

Any protein-solubilizing detergent may be used in the extraction process including, without limitation, a zwitterionic detergent such as Zwittergent™ 3-12 or Zwittergent™ 3-14, a non-ionic detergent such as Triton™ X-100, sarcosyl, a glucoside such as octyl-glucoside, nonyl-glucoside or decyl-glucoside, cholate or deoxycholate, or dodecyl-maltoside. In preferred embodiments, the detergents are Zwittergent™ 3-12, Triton™ X-100 and sarcosyl for the specific steps described herein.

The term "zwitterionic detergent" refers to a detergent that is electrically neutral overall, but has a positively charged moiety and a negatively charged moiety and is commonly used to solubilize hydrophobic proteins. The term "non-inonic detergent" refers to a molecule acting as a detergent that is uncharged.

A wide variety of compounds may be used as buffers in the extraction process, as long as the compound is not retained by the diafiltration membrane. Such buffers include, but are not limited to, Hepes, 3-(N-morpholino)propane sulfonic acid (MOPS), Tris™, sodium phosphate and sodium borate. In preferred embodiments, the buffers are Hepes, Tris™ and sodium phosphate for the specific steps described herein.

Chelating agents are used at various steps of the extraction process to prevent proteolysis and/or to sequester divalent cations. The preferred chelating agent is EDTA. Divalent cations are used at various steps of the extraction process to stabilize or to solubilize the outer membrane proteins. Divalent cations include metal ions such as magnesium and calcium ($Mg^{+2}$ and $Ca^{+2}$), with $Mg^{+2}$ being preferred. Sodium chloride is the preferred salt in the salt disruption step in the process for extracting lipidated rP6.

The extraction may be modified by including at least one unit operation with a different diafiltration membrane having a different molecular weight cut-off, such that the lysate passes first through a larger size membrane, and then through at least one smaller size membrane. Such a sequence of membranes permits the extraction process to purify two or more integral membrane proteins separately at different stages (lysates) of the same diafiltration run.

For the extraction of native or recombinantly-expressed, gram-negative inner membrane proteins from bacteria or bacterial host cells containing a recombinant vector, respectively, by differential detergent tangential flow diafiltration, a process is used which comprises:
  (a) lysing bacteria or bacterial host cells containing a recombinant vector in a fermentation broth;
  (b) diafiltering the lysed fermentation broth from (a) with a buffer which is not retained by the diafiltration membrane, wherein said buffer removes intracellular and extracellular contaminants through the permeate, and using a chelating agent to prevent proteolysis;
  (c) diafiltering the lysate from (b) with a detergent and a buffer which is not retained by the diafiltration membrane, wherein said detergent solubilizes and removes inner membrane proteins, and using a divalent cation to stabilize the outer membrane proteins, thereby preventing their solubilization; and
  (d) collecting the inner membrane proteins removed in (c).

For the extraction of native or recombinantly-expressed, gram-negative outer membrane proteins from bacteria or bacterial host cells containing a recombinant vector, respectively, by differential detergent tangential flow diafiltration, a process is used which comprises:
  (a) lysing bacteria or bacterial host cells containing a recombinant vector in a fermentation broth;
  (b) diafiltering the lysed fermentation broth from (a) with a buffer which is not retained by the diafiltration membrane, wherein said buffer removes intracellular and extracellular contaminants through the permeate, and using a chelating agent to prevent proteolysis;
  (c) diafiltering the lysate from (b) with a detegent and a buffer which is not retained by the diafiltration membrane, wherein said detergent solubilizes and removes inner membrane proteins, and using a divalent cation to stabilize the outer membrane proteins, thereby preventing their solubilization;
  (d) diafiltering the lysate from (c) with the buffer from (c), and using a divalent cation from (c) in the absence of detergent, in order to reduce the concentration of the detergent from (c);
  (e) diafiltering the lysate from (d) with a buffer which is not retained by the diafiltration membrane, a chelating agent and a detergent to solubilize and remove the outer membrane proteins; and
  (f) collecting the outer membrane proteins removed in (e).

If desired, further extraction can be performed by adding the following steps to the foregoing process:
  (g) diafiltering the lysate from (e) with reagents of (e), with the exception of the detergent, in order to reduce the concentration of the detergent;
  (h) diafiltering the lysate from (g) with reagents of (e); and
  (i) collecting the outer membrane proteins removed in (h).

For the extraction of lipidated recombinant, outer membrane protein P4 (lipidated rP4) of *H. influenzae* from bacterial host cells by differential detergent tangential flow diafiltration, a process is used which comprises:
  (a) lysing bacterial host cells in a fermentation broth;
  (b) diafiltering the lysed fermentation broth from (a) with a buffer which is not retained by the diafiltration membrane, wherein said buffer removes intracellular and extracellular contaminants through the permeate, and using a chelating agent to prevent proteolysis;
  (c) diafiltering the lysate from (b) with a detergent and a buffer which is not retained by the diafiltration membrane, wherein said detegent solubilizes and removes inner membrane proteins, and using a divalent cation to stabilize the outer membrane proteins, thereby preventing their solubilization;
  (d) diafiltering the lysate from (c) with the buffer from (c), and using a divalent cation from (c) in the absence of detergent, in order to reduce the concentration of the detergent from (c);
  (e) diafiltering the lysate from (d) with a buffer which is not retained by the diafiltration membrane, a chelating agent and a detergent to solubilize the outer membrane proteins;
  (f) diafiltering the lysate from (e) with a buffer which is not retained by the diafiltration membrane, a chelating agent and a detergent to extract and remove the lipidated rP4; and
  (g) collecting the lipidated rP4 removed in (f).

If desired, further extraction of lipidated rP4 can be performed by adding the following steps to the foregoing process:
  (h) diafiltering the lysate from (f) with reagents of (f), with the exception of the detergent, in order to reduce the concentration of the detergent;
  (i) diafiltering the lysate from (h) with reagents of (f) to extract and remove the lipidated rP4; and
  (j) collecting the lipidated rP4 removed in (i).

If also desired, still further extraction of lipidated rP4 can be performed by adding the following steps to the foregoing process:
  (k) diafiltering the lysate from (j) with reagents of (f), with the exception of the detergent, in order to reduce the concentration of the detergent;
  (l) diafiltering the lysate from (k) with reagents of (f) to extract and remove the lipidated rP4; and
  (m) collecting the lipidated rP4 removed in (l).

Still further cycles of lipidated rP4 extraction may be utilized, if desired.

For the extraction of lipidated recombinant, outer membrane protein P6 (lipidated rP6) of *H. influenzae* from bacterial host cells by differential detergent tangential flow diafiltration, a process is used which comprises:
  (a) lysing bacterial host cells in a fermentation broth;
  (b) diafiltering the lysed fermentation broth from (a) with a buffer which is not retained by the diafiltration membrane, wherein said buffer removes intracellular and extracellular contaminants through the permeate, and using a chelating agent to prevent proteolysis;
  (c) diafiltering the lysate from (b) with a detergent and a buffer which is not retained by the diafiltration membrane, wherein said detergent solubilizes and removes inner membrane proteins, and using a divalent cation to stabilize the outer membrane proteins, thereby preventing their solubilization;
  (d) diafiltering the lysate from (c) with a buffer which is not retained by the diafiltration membrane, a chelating agent to sequester divalent cation and to prevent proteolysis, and a detergent to solubilize and remove the outer membrane proteins other than lipidated rP6;

(e) diafiltering the lysate from (d) with a buffer which is not retained by the diafiltration membrane, a chelating agent to prevent proteolysis, a detergent to remove additional outer membrane proteins, and a salt to disrupt the membrane/outer membrane protein complex;

(f) diafiltering the lysate from (e) with reagents of (e), with the exception of the detergent and the salt, in order to reduce the concentration of the detergent;

(g) diafiltering the lysate from (f) with a detergent and a buffer which is not retained by the diafiltration membrane, wherein said detergent solubilizes and removes additional proteins bound to the cellular outer membrane, and using a chelating agent to prevent proteolysis;

(h) diafiltering the lysate from (g) with the buffer from (g) and the chelating agent of (g) to reduce the concentration of the detergent from (g);

(i) diafiltering the lysate from (h) with a phosphate compound and a detergent to solubilize and remove additional proteins bound to the cellular outer membrane;

(j) diafiltering the lysate from (i) with a phosphate compound to reduce the concentration of the detergent from (i);

(k) heating the lysate from (j) to remove lipidated rP6 from the membrane while diafiltering that lysate with a phosphate compound and a detergent to solubilize, extract and remove the lipidated rP6; and (l) collecting the lipidated rP6 removed in (k).

If desired, the process for extracting lipidated rP6 may be modified by concentrating the lysate from (j) before proceeding to (k).

In order that this invention may be better understood, the following examples are set forth. The examples are for the purpose of illustration only and are not to be construed as limiting the scope of the invention.

EXAMPLES

Example 1

Lipidated rP4 Differential

Detergent Membrane Extraction

The overall process for extracting lipidated rP4 from bacterial cells, such as *E. coli* cells, involved microfluidization or cell lysis and membrane differential detergent extraction. The fermentation broth was harvested and adjusted to 5 mM EDTA to inhibit possible protein degradation from metalloproteases. The broth was then diluted to less than 5% w/v wet cell weight concentration and lysed with a high-pressure microfluidizer (Microfluidics, Newton, Mass.). The lysed cells were diafiltered with a specific sequence of buffer solutions using a tangential flow system that includes 1000 kD regenerated cellulose Millipore membranes of surface area 0.002 m$^2$/g wet weight cells. The sequence of buffer solutions was chosen to solubilize inner membrane proteins first and then to solubilize outer membrane proteins which includes rP4. During diafiltration, the solubilized proteins of approximate size less than the molecular weight cut-off of the membrane passed through the permeate, while larger molecules and unsolubilized proteins were retained. The sequence of diafiltration steps was as follows:

(1) The lysed fermentation broth was diafiltered with 10 mM Hepes/1 mM EDTA/pH 8.0 at a volume equal to three times the volume of the retentate to remove intracellular and extracellular contaminants through the permeate.

(2) The lysate was diafiltered five times with 10 mM Hepes/1 mM MgCl$_2$/1% Triton™ X-100, pH 8, to solubilize and remove inner membrane proteins. The Mg$^{+2}$ ions stabilized the outer membrane; therefore, the outer membrane proteins were not solubilized in the presence of Triton™ X-100.

(3) The lysate was diafiltered three times with 10 mM Hepes/1 mM MgCl$_2$/pH 8, to reduce the Triton™ X-100 concentration.

(4) The lysate was diafiltered three times with 50 mM Tris™/5 mM EDTA/1% Zwittergent™ 3-12/pH 8, to solubilize the outer membrane proteins, including lipidated rP4, and then to begin extracting and collecting lipidated rP4 from the outer membrane.

(5) The lysate was diafiltered three times with 50 mM Tris™/5 mM EDTA, pH 8. This step was performed without Zwittergent™ 3-12, because zwitterionic detergents do not pass through the 1000 kD cut-off membrane as readily as smaller compounds such as salts. This step served to reduce the Zwittergent™ 3-12 concentration in the membrane; the Zwittergent™ 3-12 concentration of step (4) would otherwise reduce the flow rate through the membrane during steps (6) and (8) below.

(6) The lysate was diafiltered two times with 50 mM Tris™/5 mM EDTA/1% Zwittergent™ 3-12, pH 8, to continue extracting and collecting lipidated rP4 from the outer membrane.

(7) The lysate was diafiltered two times with 50 mM Tris™/5 mM EDTA, pH 8 to again reduce the Zwittergent™ 3-12 concentration.

(8) The lysate was diafiltered two times with 50 mM Tris™/5=M EDTA/1% Zwittergent™ 3-12, pH 8 to continue extracting and collecting lipidated rP4 from the outer membrane.

(9) The lysate was diafiltered two times with 50 mM Tris™/5 mM EDTA, pH 8 to again reduce the Zwittergent™ 3-12 concentration.

During the diafiltration steps, the transmembrane pressure was maintained at approximately 5 psi and the cross flow rate was maintained at 150 liters/meters$^2$ membrane area/hour (lmh). The diafiltration processes were run at room temperature. The permeate flux ranged from 30 to 40 lmh, which was sufficiently high for the extraction process to be practical and scalable.

During the extraction, samples were taken at various points for analysis by SDS-PAGE to evaluate the effect of various diafiltration steps on the extraction of proteins. Samples were precipitated by alcohol addition, centrifuged, and then resolubilized at 20% of the original volume in SDS sample preparation buffer. This method of preparing samples concentrated the sample and reduced the Triton™ X-100 or Zwittergent™ 3-12 concentration of the samples. Triton™ X-100 or Zwittergent™ 3-12 interferes with the binding of SDS to the sample and reduces the resolution of bands on gels. Ten µl of each sample was loaded on to Novex (Encinitas, Calif.) 10% acrylamide gels and the gels were run for 60-90 minutes at 125 Volts.

A typical SDS-PAGE analysis of the samples taken from the permeate streams during the extraction process for lipidated rP4 is shown in FIG. 1. Lipidated rP4 ran at approximately 30 kD on these gels. The gel shows that some contaminating proteins were removed during diafiltration with lysis buffer (lane 5) and buffer containing Triton™ X-100 (lane 6). There was very little loss of lipidated rP4 during these diafiltration steps. During the Zwittergent™ 3-12 diafiltration step, lipidated rP4 was extracted in a partially purified state (lane 8). At the end of the Zwittergent™ 3-12 diafiltration step, very little lipidated rP4 was present in the permeate stream (lane 9). This indicated that most of the solubilized lipidated rP4 had been recovered through the permeate. Other experiments have shown that very little unsolubilized lipidated rP4 remains in the retentate after the completion of the extraction process (data not shown). The 30 kD band of the Zwittergent™ 3-12 extract has been shown to be lipidated rP4 by western analysis (data not shown).

tion. This data also showed that the total recovery of lipidated rP4 protein in the extraction pool as compared to the cell lysate was 18%.

The results are shown in Table 1:

TABLE 1

| Sample | Volume L | Protein mg/ml | Total Protein g | % LrP4 | LrP4 g/L | LrP4 g | % Reduction in LrP4 | % LrP4 Recovered |
|---|---|---|---|---|---|---|---|---|
| N21001 Cell Lysate | 10 | 20.00 | 200.00 | 13.70 | 2.74 | 27.40 | | |
| N21002 Cell Lysate | 10 | 10.80 | 108.00 | 12.10 | 1.31 | 13.07 | | |
| N21003 Cell Lysate | 10 | 11.20 | 112.00 | 11.90 | 1.33 | 13.33 | | |
| N21004 Cell Lysate | 10 | 7.80 | 78.00 | 12.60 | 0.98 | 9.83 | | |
| N21001 Extracted Cell Lysate | 10 | 2.60 | 26.00 | 14.80 | 0.38 | 3.85 | 85.96% | 14.04% |
| N21002 Extracted Cell Lysate | 10 | 1.30 | 13.00 | 12.40 | 0.16 | 1.61 | 87.66% | 12.34% |
| N21003 Extracted Cell Lysate | 10 | 1.20 | 12.00 | 13.40 | 0.16 | 1.61 | 87.94% | 12.06% |
| N21004 Extracted Cell Lysate | 10 | 3.40 | 34.00 | 14.30 | 0.49 | 4.86 | 50.53% | 49.47% |
| N21001 Extraction Pool | 120 | 0.06 | 7.20 | 56.30 | 0.03 | 4.05 | | 14.79% |
| N21002 Extraction Pool | 120 | 0.06 | 6.60 | 42.30 | 0.02 | 2.79 | | 21.36% |
| N21003 Extraction Pool | 120 | 0.03 | 3.12 | 73.60 | 0.02 | 2.30 | | 17.23% |
| N21004 Extraction Pool | 120 | 0.05 | 6.24 | 29.90 | 0.02 | 1.87 | | 18.98% |

Example 2

Additional Extraction Runs for Lipidated rP4

This Example presents data generated from four additional extraction runs for lipidated rP4. In each run, a recombinant E. coli fermentation broth was first adjusted to 5 mM EDTA to inhibit possible protein degradation from metalloproteases. The fermentation broth was then adjusted to a wet cell concentration of ten percent and lysed by passing through a Microfluidics microfluidizer. This cell lysate was then aliquoted into portions containing an equivalent of 500 grams of cells and frozen at −70° C.

A 500 gram portion of lysed E. coli fermentation broth was then removed from −70° C. and thawed in a water bath at a temperature not greater than 40° C. The cell lysate was then diluted to five percent wet cell weight. This five percent cell lysate was then subjected to the differential detergent extraction process utilizing tangential flow diafiltration as described in Example 1. The only slight difference was that in step (4) the diafiltration was conducted twice rather than three times.

Figure 2:
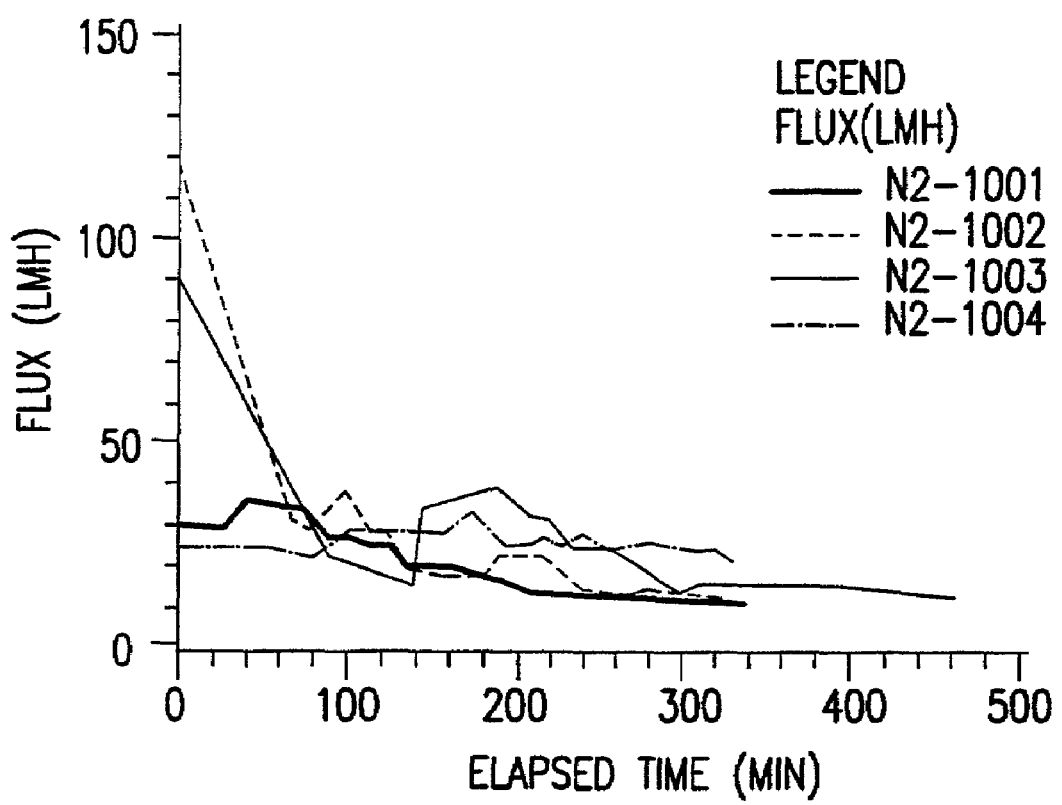
FIG. 2 depicts the permeate flux from four runs over the time course of the extraction process for lipidated rP4, as described in Example 2 below. The flux is measured in liters/meters$^2$ membrane area/hour (lmh).

SDS-PAGE analysis of samples taken at various points during the extraction gave results comparable to those seen in FIG. 1 (data not shown). The amount of lipidated rP4 recovered in each of the four runs was calculated. The percent lipidated rP4 was determined in the cell lysate before and after extraction by running samples on SDS-PAGE gels and then scanning them on a densitometer. This data illustrated that there was an average reduction in grams of 78% of lipidated rP4 protein in the cell lysate before and after extrac- The reproducibility of the diafiltration process is illustrated in FIG. 2. The permeate flux from the four runs over the course of the extraction process was monitored. The similarity in the flux rates throughout the process demonstrates that the extraction process is controllable and reproducible.

To purify the extracted lipidated rP4, the lipidated rP4-containing cell lysate extract was then processed through tandem ion exchange columns consisting of a DEAE Sepharose™ Fast Flow and a SP Sepharose™ Fast Flow column (Pharmacia & Upjohn, Piscataway, N.J.). The columns were washed with additional equilibration buffer and the DEAE column was then removed from the process stream. The SP column was then washed with 20 column volumes of equilibration buffer and then eluted with a NaCl step gradient, yielding purified LrP4 30K protein. The 20 mM NaCl concentration eluted a purified aggregated form of lipidated rP4 protein (Form I). The 140 mM NaCl concentration eluted a mixture of aggregated and non-aggregated form of lipidated rP4 protein (Form II).

The Form II lipidated rP4 30K protein was then converted to the more aggregated Form I state by subjecting the protein to a controlled slow freezing. The two purified forms may be purified and stored separately, or may be purified separately and then combined. The conversion process was as follows:
(1) Obtain sterile filtered aliquots of lipidated rP4 Form II.
(2) Slow freeze to −6° C.

Example 3

Lipidated rP6 Differential

Detergent Membrane Extraction

The process for extracting lipidated rP6 was similar to the process for extracting lipidated rP4. However, the diafiltration process required more steps because lipidated rP6 is tightly associated with peptidoglycans. The fermentation broth of E. coli cells expressing lipidated rP6 was adjusted to 10 mM EDTA and diluted to less than or equal to 10% wet weight cells/volume prior to homogenization. The cells were then lysed with a high-pressure microfluidizer and diafiltered at room temperature with a sequence of buffers using a cross-flow membrane filtration device. It was determined that the minimum membrane area to allow efficient mass transport of solubilized proteins through the membrane was approximately 0.002 m$^2$/g wet weight cells. The solubilized proteins of approximate size less than the 1000 kD molecular weight cut-off rating of the membrane passed through with the permeate, while larger molecules and unsolubilized proteins were retained. The sequence of diafiltration steps was as follows:

(1) The lysed fermentation broth was diafiltered with 10 mM Hepes/1 mM EDTA/pH 8.0 (lysis buffer) at a volume equal to three times the volume of the retentate to remove intracellular and extracellular contaminants through the permeate.

(2) The lysate was diafiltered three times with 10 mM Hepes/1 mM MgCl$_2$/0.2% Triton™ X-100 to solubilize and remove inner membrane proteins. The Mg$^{+2}$ ions stabilized the outer membrane; therefore, the outer membrane proteins were not solubilized in the presence of Triton™ X-100.

(3) The lysate was diafiltered three times with 50 mM Tris™/5 mM EDTA/0.2% Zwittergent™ 3-14 to solubilize and remove other outer membrane proteins (but not lipidated rP6). The EDTA serves to sequester the Mg$^{+2}$ ions from step (2), as well as to prevent proteolysis.

(4) The lysate was diafiltered three times with 50 mM Tris™/5 mM EDTA/0.5 M NaCl/0.2% Zwittergent™ 3-14 to solubilize and remove additional proteins. NaCl was added to the buffer in this step to disrupt any ionic interactions between membrane proteins and membranes. This step was performed because lipidated rP6 is a peptidoglycan-associated lipoprotein, and the salt serves to remove membrane-bound proteins (but not lipidated rP6) from the membrane/outer membrane protein complex (lipidated rP4 is not so associated; thus this step was not performed for extracting that protein). The diafiltration was continued with three retentate volumes of 50 mM Tris™/5 mM EDTA to reduce the Zwittergent™ 3-14 concentration in the retentate.

(5) The lysate was diafiltered three times with 50 mM Tris™/5 mM EDTA/0.2% sarcosyl to remove additional membrane-bound proteins (but not lipidated rP6) and then diafiltered three times with 50 mM Tris™/5 mM EDTA to reduce the sarcosyl concentration in the retentate.

(6) The lysate was diafiltered three times with 10 mM sodium phosphate/0.2% Zwittergent™ 3-12 to remove additional membrane-bound proteins (but not lipidated rP6), and then diafiltered three times with 10 mM sodium phosphate to reduce the Zwittergent™ 3-12 concentration in the retentate.

(7) The lysate was concentrated to 20% of its original volume and then diafiltered three times with 10 mM sodium phosphate/0.2% Zwittergent™ 3-12 at 55° C. to solubilize lipidated rP6, which was collected through the permeate. The concentration was performed prior to diafiltration to increase the concentration of lipidated rP6 in the permeate. The diafiltration was continued for three additional retentate volumes with 10 mM sodium phosphate at 55° C. to reduce the Zwittergent™ 3-12 concentration in the retentate. This heating step was performed because (as in step (4) above)) lipidated rP6 is a peptidoglycan-associated lipoprotein, and heating serves to remove lipidated rP6 from the membrane/membrane protein complex (lipidated rP4 is not so associated; thus this step was not performed for extracting that protein). Finally, the diafiltration was concluded with three retentate volumes of 10 mM sodium phosphate at 55° C.

During the diafiltration steps, the transmembrane pressure was maintained at approximately 10 psi and the cross flow rate was maintained at approximately 120-180 lmh. All the diafiltration processes were run at room temperature, except the final 55° C. extraction step, which was run at the higher temperature to solubilize lipidated rP6. The permeate flux ranged from 30 to 50 lmh, which was sufficiently high for the extraction process to be practical and scalable.

During the extraction, samples were taken at various points for analysis by SDS-PAGE to evaluate the effect of various diafiltration steps on the extraction of proteins. Samples were prepared and run on gels as described in Example 1.

Figure 3:
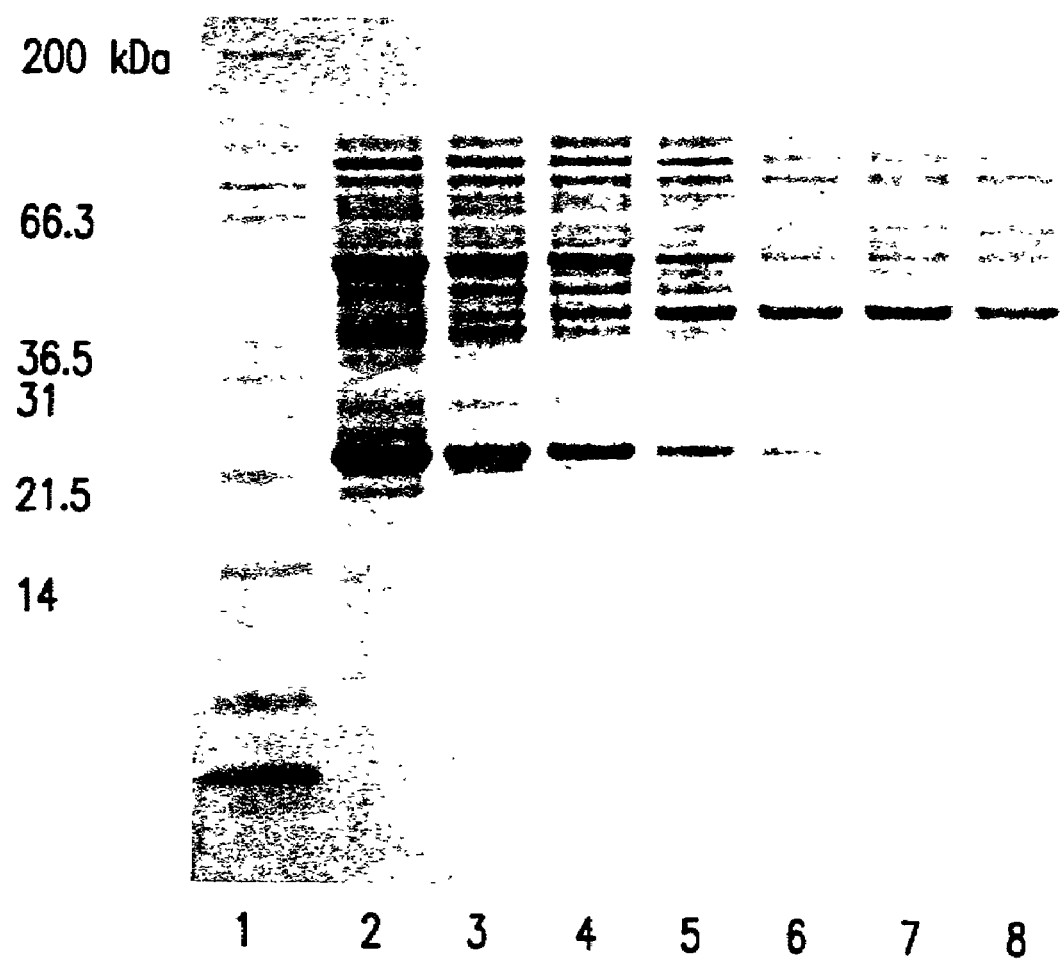
FIG. 3 depicts an SDS-PAGE analysis of samples taken from the permeate streams during the first part of the extraction process for lipidated rP6, as described in Example 3 below. Lanes: 1—Mark 12 standard; 2—permeate from diafiltration with lysis buffer; 3—Permeate from diafiltration with Triton™ X-100; 4—Permeate from diafiltration with Tris™ buffer; 5—Permeate from diafiltration with n-Tetradecyl-N,N-dimethyl-3-ammonio-1-propanesulfonate (Zwittergent™ 3-14); 6—Permeate from diafiltration with Zwittergent™ 3-14/0.5 M NaCl; 7—Permeate from diafiltration with Tris™ buffer; 8—Permeate from diafiltration with Sarcosyl.
Figure 4:
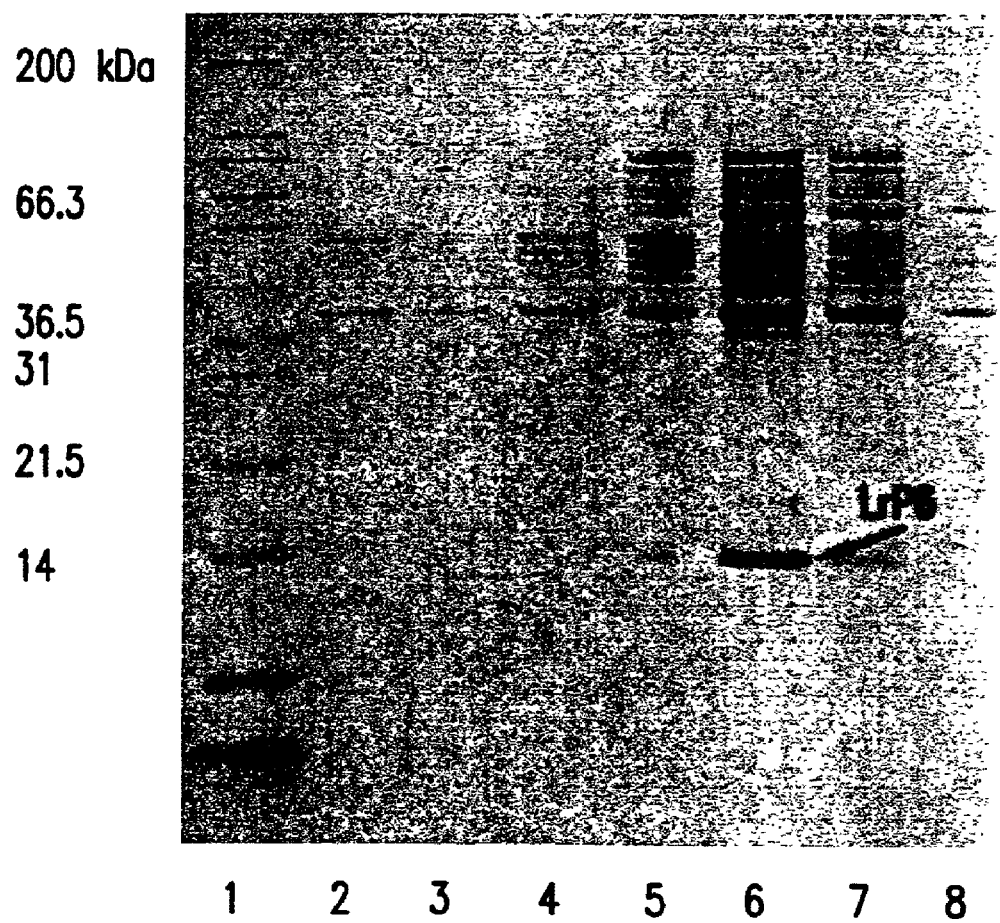
FIG. 4 depicts an SDS-PAGE analysis of samples taken from the permeate streams during the second part of the extraction process for lipidated rP6, as described in Example 3 below. Lanes: 1—Mark 12 Standard; 2—Permeate from diafiltration with Tris™ buffer; 3-Permeate from diafiltration with Zwittergent™ 3-12 at room temperature; 4—Permeate from diafiltration with Tris™ buffer; 5—Permeate from concentration step; 6—Permeate from diafiltration with Zwittergent™ 3-12 at 55° C.; 7-Permeate from diafiltration with Tris™ buffer at 55° C.; 8—Permeate from diafiltration with Zwittergent™ 3-12 at 55° C.

A typical SDS-PAGE analysis of the samples taken from the permeate streams during the extraction process of lipidated rP6 is shown in FIGS. 3 and 4. Lipidated rP6 ran at approximately 15 kD on these gels. The gels showed that some contaminating proteins are removed during diafiltration with the lysis buffer (FIG. 3, lane 2) and buffer containing various detergents (FIG. 3, lanes 5-6 and FIG. 4, lane 3). There was very little loss of lipidated rP6 during these diafiltration steps. During the final Zwittergent™ 3-12 diafiltration step at 55° C., lipidated rP6 was extracted in a partially purified state (FIG. 4, lane 6). At the end of the second Zwittergent™ 3-12 diafiltration step at 55° C., very little lipidated rP6 was present in the permeate stream (FIG. 4, lane 8). This suggested that most of the solubilized lipidated rP6 had been recovered through the permeate. Other experiments have shown that very little lipidated rP6 remains unsolubilized in the retentate after the completion of the diafiltration process (data not shown). The 15 kD band of the Zwittergent™ 3-12/55° C. extract has been shown to be lipidated rP6 by western analysis (data not shown).

The process described above was repeated to extract lipidated rP6 from the broth of another E. coli fermentation. The SDS-PAGE analysis was similar to that seen in FIGS. 3 and 4 (data not shown), and the 15 kD band of the Zwittergent™ 3-12/55° C. extract was again shown to be lipidated rP6 by western analysis (data not shown).

Example 4

Additional Extraction Runs for Lipidated rP6

This Example presents data generated from three additional extraction runs for lipidated rP6. In each run, the process described in Example 3 was used to extract lipidated rP6 from a recombinant E. coli fermentation broth.

The results are shown in Table 2:

TABLE 2

| Sample (15 ml) | Volume L | Protein mg/ml | Total Protein g | Purity % | Total LrP6 g |
|---|---|---|---|---|---|
| N4-1002 Lysed Fermentation Broth | 5 | 18.70 | 93.50 | 10.70% | 10.00 |
| N4-1002 55C Extraction Pool | 20 | 0.17 | 3.43 | 34.20% | 1.17 |
| N4-1003 Lysed Fermentation Broth | 5 | 14.74 | 73.71 | 2.30% | 1.70 |
| N4-1003 55C Extraction Pool | 20 | 0.73 | 14.52 | 19.50% | 2.83 |
| N4-1004 Lysed Fermentation Broth | 5 | 14.74 | 73.71 | 7.20% | 5.31 |
| N4-1004 55C Extraction Pool | 20 | 0.08 | 1.66 | 26.00% | 0.43 |

TABLE 2-continued

| Sample (15 ml) | Volume L | Protein mg/ml | Total Protein g | Purity % | Total LrP6 g |
|---|---|---|---|---|---|

What is claimed is:

1. A process for extracting native or recombinantly-expressed, gram-negative inner membrane proteins from bacteria or bacterial host cells containing a recombinant vector by differential detergent tangential flow diafiltration, which comprises:
   (a) lysing bacteria or bacterial host cells containing a recombinant vector in a fermentation broth;
   (b) diafiltering the lysed fermentation broth from (a) with a buffer which is not retained by the diafiltration membrane, wherein said buffer removes intracellular and extracellular contaminants through the permeate, and using a chelating agent to prevent proteolysis;
   (c) diafiltering the lysate from (b) with a detergent and a buffer which is not retained by the diafiltration membrane, wherein said detergent solubilizes and removes inner membrane proteins, and using a divalent cation to stabilize the outer membrane proteins, thereby preventing their solubilization; and
   (d) collecting the inner membrane proteins removed in (c).

2. The process of claim 1 wherein: the lysis of (a) occurs in a microfluidizer; in (b), the buffer is selected from the group consisting of Hepes, 3-(N-morpholino)propane sulfonic acid (MOPS), Tris(hydroxymethyl)aminomethane, sodium phosphate and sodium borate; and in (c), the buffer is selected from the group consisting of Hepes, MOPS, Tris(hydroxymethyl)aminomethane, sodium phosphate and sodium borate, the detergent is selected from the group consisting of a zwitterionic detergent, a non-ionic detergent, sarcosyl, a glucoside compound, a cholate compound and dodecyl-maltoside, and the divalent cation is selected from the group consisting of magnesium and calcium ($Mg^{+2}$ and $Ca^{+2}$).

3. The process of claim 2 wherein in (b), the buffer is Hepes and the chelating agent is EDTA; and in (c), the buffer is Hepes, the detergent is alpha-[4-(1,1,3,3,-tetramethylbutyl) phenyl]-omega-hydroxypoly(oxy-1,2-ethanediyl), and the divalent cation is $Mg^{+2}$.

4. A process for extracting native or recombinantly-expressed, gram-negative outer membrane proteins from bacteria or bacterial host cells containing a recombinant vector by differential detergent tangential flow diafiltration, which comprises:
   (a) lysing bacteria or bacterial host cells containing a recombinant vector in a fermentation broth;
   (b) diafiltering the lysed fermentation broth from (a) with a buffer which is not retained by the diafiltration membrane, wherein said buffer removes intracellular and extracellular contaminants through the permeate, and using a chelating agent to prevent proteolysis;
   (c) diafiltering the lysate from (b) with a detergent and a buffer which is not retained by the diafiltration membrane, wherein said detergent solubilizes and removes inner membrane proteins, and using a divalent cation to stabilize the outer membrane proteins, thereby preventing their solubilization;
   (d) diafiltering the lysate from (c) with the buffer from (c), and using a divalent cation from (c) in the absence of detergent, in order to reduce the concentration of the detergent from (c);
   (e) diafiltering the lysate from (d) with a buffer which is not retained by the diafiltration membrane, a chelating agent and a detergent to solubilize and remove the outer membrane proteins; and
   (f) collecting the outer membrane proteins removed in (e).

5. The process of claim 4 wherein: the lysis of (a) occurs in a microfluidizer; in (b), the buffer is selected from the group consisting of Hepes, MOPS, Tris(hydroxymethyl)aminomethane, sodium phosphate and sodium borate; in (c), the buffer is selected from the group consisting of Hepes, MOPS, Tris(hydroxymethyl)aminomethane, sodium phosphate and sodium borate, the detergent is selected from the group consisting of a zwitterionic detergent, a non-ionic detergent, sarcosyl, a glucoside compound, a cholate compound and dodecyl-maltoside, and the divalent cation is selected from the group consisting of $Mg^{+2}$ and $Ca^{+2}$; in (d), the buffer is selected from the group consisting of Hepes, MOPS, Tris (hydroxymethyl)aminomethane, sodium phosphate and sodium borate, and the divalent cation is selected from the group consisting of $Mg^{+2}$ and $Ca^{+2}$; and in (e), the buffer is selected from the group consisting of Hepes, MOPS, Tris (hydroxymethyl)aminomethane, sodium phosphate and sodium borate, and the detergent is selected from the group consisting of a zwitterionic detergent, a non-ionic detergent, sarcosyl, a glucoside compound, a cholate compound and dodecyl-maltoside.

6. The process of claim 4 wherein in (b), the buffer is Hepes and the chelating agent is EDTA; in (c), the buffer is Hepes, the detergent is alpha-[4-(1,1,3,3,-tetramethylbutyl)phenyl]-omega-hydroxypoly(oxy-1,2-ethanediyl), and the divalent cation is $Mg^{+2}$; in (d), the buffer is Hepes and the divalent cation is $Mg^{+2}$; and in (e), the buffer is Tris(hydroxymethyl) aminomethane, the chelating agent is EDTA, and the detergent is n-Dodecyl-N,N-dimethyl-3-ammonio-1-propane-sulfonate.

7. The process of claim 4, which further comprises:
   (g) diafiltering the lysate from (e) with reagents of (e), with the exception of the detergent, in order to reduce the concentration of the detergent;
   (h) diafiltering the lysate from (g) with reagents of (e); and
   (i) collecting the outer membrane proteins removed in (h).

8. A process for extracting lipidated recombinant outer membrane protein P4 (rP4) of *Haemophilus influenzae* from bacterial host cells by differential detergent tangential flow diafiltration, which comprises:
   (a) lysing bacterial host cells in a fermentation broth;
   (b) diafiltering the lysed fermentation broth from (a) with a buffer which is not retained by the diafiltration membrane, wherein said buffer removes intracellular and extracellular contaminants through the permeate, and using a chelating agent to prevent proteolysis;
   (c) diafiltering the lysate from (b) with a detergent and a buffer which is not retained by the diafiltration membrane, wherein said detergent solubilizes and removes inner membrane proteins, and using a divalent cation to stabilize the outer membrane proteins, thereby preventing their solubilization;
   (d) diafiltering the lysate from (c) with the buffer from (c), and using a divalent cation from (c) in the absence of detergent, in order to reduce the concentration of the detergent from (c);
   (e) diafiltering the lysate from (d) with a buffer which is not retained by the diafiltration membrane, a chelating agent and a detergent to solubilize the outer membrane proteins;

(f) diafiltering the lysate from (e) with a buffer which is not retained by the diafiltration membrane, a chelating agent and a detergent to extract and remove the lipidated rP4; and (g) collecting the lipidated rP4 removed in (f).

9. The process of claim 8 wherein: the lysis of (a) occurs in a microfluidizer; in (b), the buffer is selected from the group consisting of Hepes, MOPS, Tris(hydroxymethyl)aminomethane, sodium phosphate and sodium borate; in (c), the buffer is selected from the group consisting of Hepes, MOPS, Tris(hydroxymethyl)aminomethane, sodium phosphate and sodium borate, the detergent is selected from the group consisting of a zwitterionic detergent, a non-ionic detergent, sarcosyl, a glucoside compound, a cholate compound and dodecyl-maltoside, and the divalent cation is selected from the group consisting of $Mg^{+2}$ and $Ca^{+2}$; in (d), the buffer is selected from the group consisting of Hepes, MOPS, Tris(hydroxymethyl)aminomethane, sodium phosphate and sodium borate, and the divalent cation is selected from the group consisting of $Mg^{+2}$ and $Ca^{+2}$; in (e), the buffer is selected from the group consisting of Hepes, MOPS, Tris(hydroxymethyl)aminomethane, sodium phosphate and sodium borate, and the detergent is selected from the group consisting of a zwiitterionic detergent, a non-ionic detergent, sarcosyl, a glucoside compound, a cholate compound and dodecyl-maltoside; and in (f), the buffer is selected from the group consisting of Hepes, MOPS, Tris(hydroxymethyl)aminomethane, sodium phosphate and sodium borate, and the detergent is selected from the group consisting of a zwitterionic detergent, a non-ionic detergent compound, sarcosyl, a glucoside compound, a cholate compound and dodecyl-maltoside.

10. The process of claim 9 wherein in (b), the buffer is Hepes and the chelating agent is EDTA; in (c), the buffer is Hepes, the detergent is alpha-[4-(1,1,3,3,-tetramethylbutyl) phenyl]-omega-hydroxypoly(oxy-1,2-ethanediyl), and the divalent cation is $Mg^{+2}$; in (d), the buffer is Hepes and the divalent cation is $Mg^{+2}$; in (e), the buffer is Tris(hydroxymethyl)aminomethane, the chelating agent is EDTA, and the detergent is n-Dodecyl-N,N-dimethyl-3-ammonio-1-propanesulfonate; and in (f), the buffer is Tris(hydroxymethyl)aminomethane, the chelating agent is EDTA, and the detergent is n-Dodecyl-N,N-dimethyl-3-ammonio-1-propanesulfonate.

11. The process of claim 8, which further comprises:

(h) diafiltering the lysate from (f) with reagents of (f), with the exception of the detergent, in order to reduce the concentration of the detergent;

(i) diafiltering the lysate from (h) with reagents of (f to extract and remove the lipidated rP4; and (l) collecting the lipidated rP4 removed in (i).

12. The process of claim 11, which further comprises:

(k) diafiltering the lysate from (j) with reagents of (f), with the exception of the detergent, in order to reduce the concentration of the detergent;

(l) diafiltering the lysate from (k) with reagents of (f) to extract and remove the lipidated rP4; and (m) collecting the lipidated rP4 removed in (l).

13. A process for extracting lipidated recombinant outer membrane protein P6 (rP6) of *Haemophilus influenzae* from bacterial host cells by differential detergent tangential flow diafiltration, which comprises:

(a) lysing bacterial host cells in a fermentation broth;

(b) diafiltering the lysed fermentation broth from (a) with a buffer which is not retained by the diafiltration membrane, wherein said buffer removes intracellular and extracellular contaminants through the permeate, and using a chelating agent to prevent proteolysis;

(c) diafiltering the lysate from (b) with a detergent and a buffer which is not retained by the diafiltration membrane, wherein said detergent solubilizes and removes inner membrane proteins, and using a divalent cation to stabilize the outer membrane proteins, thereby preventing their solubilization;

(d) diafiltering the lysate from (c) with a buffer which is not retained by the diafiltration membrane, a chelating agent to sequester divalent cation and to prevent proteolysis, and a detergent to solubilize and remove the outer membrane proteins other than lipidated rP6;

(e) diafiltering the lysate from (d) with a buffer which is not retained by the diafiltration membrane, a chelating agent to prevent proteolysis, a detergent to remove additional outer membrane proteins, and a salt to disrupt the membrane/outer membrane protein complex;

(f) diafiltering the lysate from (e) with reagents of (e), with the exception of the detergent and the salt, in order to reduce the concentration of the detergent;

(g) diafiltering the lysate from (f) with a detergent and a buffer which is not retained by the diafiltration membrane, wherein said detergent solubilizes and removes additional proteins bound to the cellular outer membrane, and using a chelating agent to prevent proteolysis;

(h) diafiltering the lysate from (g) with the buffer from (g) and the chelating agent of (g) to reduce the concentration of the detergent from (g);

(i) diafiltering the lysate from (h) with a phosphate compound and a detergent to solubilize and remove additional proteins bound to the cellular outer membrane;

(j) diafiltering the lysate from (i) with a phosphate compound to reduce the concentration of the detergent from (i);

(k) heating the lysate from (j) to remove lipidated rP6 from the membrane while diafiltering that lysate with a phosphate compound and a detergent to solubilize, extract and remove the lipidated rP6; and (l) collecting the lipidated rP6 removed in (k).

14. The process of claim 13 wherein: the lysis of (a) occurs in a microfluidizer; in (b), the buffer is selected from the group consisting of Hepes, MOPS, Tris(hydroxymethyl)aminomethane, sodium phosphate and sodium borate, and the divalent cation is selected from the group consisting of $Mg^{+2}$ and $Ca^{+2}$; in (c), the buffer is selected from the group consisting of Hepes, MOPS, Tris(hydroxymethyl)aminomethane, sodium phosphate and sodium borate, the detergent is selected from the group consisting of a zwitterionic detergent, a non-ionic detergent, sarcosyl, a glucoside compound, a cholate compound and dodecyl-maltoside, and the divalent cation is selected from the group consisting of $Mg^{+2}$ and $Ca^{+2}$; in (d), the buffer is selected from the group consisting of Hepes, MOPS, Tris(hydroxymethyl)aminomethane, sodium phosphate and sodium borate, and the detergent is selected from the group consisting of a zwitterionic detergent, a non-ionic detergent, sarcosyl, a glucoside compound, a cholate compound and dodecyl-maltoside; in (e), the buffer is selected from the group consisting of Hepes, MOPS, Tris(hydroxymethyl)aminomethane, sodium phosphate and sodium borate, the salt is a sodium salt, and the detergent is selected from the group consisting of a zwitterionic detergent, a non-ionic detergent, sarcosyl, a glucoside compound, a cholate compound and dodecyl-maltoside; in (f), the buffer is selected from the group consisting of Hepes, MOPS, Tris(hydroxymethyl)aminomethane, sodium phosphate and sodium borate; in (g), the buffer is selected from the group consisting of Hepes, MOPS, Tris(hydroxymethyl)aminomethane, sodium phosphate and sodium borate, and the detergent is selected from the group consisting of a zwitterionic detergent, a non-ionic detergent, sarcosyl, a glucoside compound, a cholate compound and dodecyl-maltoside; in (h), the buffer is selected from the group consisting of Hepes, MOPS, Tris(hydroxymethyl)aminomethane, sodium phosphate and sodium borate; in (i), the detergent is selected from the group consisting of a zwitterionic detergent, a non-ionic detergent, sarcosyl, a glucoside compound, a cholate compound and dodecyl-maltoside; and in (k), the detergent is selected from the group consisting of a zwitterionic detergent, a non-ionic detergent, sarcosyl, a glucoside compound, a cholate compound and dodecyl-maltoside.

15. The process of claim 14 wherein in (b), the buffer is Hepes and the chelating agent is EDTA; in (c), the buffer is Hepes, the detergent is alpha-[4-(1,1,3,3,-tetramethylbutyl)phenyl]-omega-hydroxypoly(oxy-1,2-ethanediyl), and the divalent cation is $Mg^{+2}$; in (d), the buffer is Hepes, the chelating agent is EDTA, and the detergent is n-Tetradecyl-N,N-dimethyl-3-ammonio-1-propanesulfonate; in (e), the buffer is Hepes, the chelating agent is EDTA, the salt is sodium chloride, and the detergent is n-Tetradecyl-N,N-dimethyl-3-ammonio-1-propanesulfonate; in (f), the buffer is Tris(hydroxymethyl)aminomethane and the chelating agent is EDTA; in (g), the buffer is Tris(hydroxymethyl)aminomethane, the detergent is sarcosyl, and the chelating agent is EDTA; in (h), the buffer is Tris(hydroxymethyl)aminomethane and the chelating agent is EDTA; in (i), the detergent is n-Dodecyl-N,N-dimethyl-3-ammonio-1-propanesulfonate, and the phosphate is sodium phosphate; in (j), the phosphate is sodium phosphate; and in (k), the detergent is n-Dodecyl-N,N-dimethyl-3-ammonio-1-propanesulfonate.

16. The process of claim 13 wherein prior to (k), the lysate from (j) is concentrated.

* * * * *

UNITED STATES PATENT AND TRADEMARK OFFICE
CERTIFICATE OF CORRECTION

PATENT NO.       : 7,553,634 B1
APPLICATION NO.  : 10/019163
DATED            : June 30, 2009
INVENTOR(S)      : Lakhotia et al.

Page 1 of 1

It is certified that error appears in the above-identified patent and that said Letters Patent is hereby corrected as shown below:

On the Title Page
Directly before Item (51), add the following two lines:
          Related U.S. Application Data
Item (60) Provisional application No. 60/141,067, filed June 25, 1999.

Column 17, line 24, change "zwiiterionic" to --zwitterionic--.

Signed and Sealed this

Eleventh Day of August, 2009

David J. Kappos
*Director of the United States Patent and Trademark Office*

UNITED STATES PATENT AND TRADEMARK OFFICE
CERTIFICATE OF CORRECTION

PATENT NO. : 7,553,634 B2  Page 1 of 1
APPLICATION NO. : 10/019163
DATED : June 30, 2009
INVENTOR(S) : Lakhotia et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 743 days.

Delete the phrase "by 743 days" and insert -- by 1,290 days --

Signed and Sealed this

Twenty-seventh Day of April, 2010

David J. Kappos
*Director of the United States Patent and Trademark Office*